US011324966B2

(12) United States Patent
Enger et al.

(10) Patent No.: US 11,324,966 B2
(45) Date of Patent: May 10, 2022

(54) DELIVERY SYSTEM FOR INTENSITY MODULATED HIGH DOSE RATE BRACHYTHERAPY WITH INTERMEDIATE ENERGY BRACHYTHERAPY ISOTOPES

(71) Applicant: THE ROYAL INSTITUTION FOR THE ADVANCEMENT OF LEARNING / MCGILL UNIVERSITY, Montréal (CA)

(72) Inventors: Shirin Abbasi Nejad Enger, Montreal (CA); Gabriel Famulari, Laval (CA)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 404 days.

(21) Appl. No.: 16/471,703

(22) PCT Filed: Dec. 20, 2017

(86) PCT No.: PCT/CA2017/051547
§ 371 (c)(1),
(2) Date: Jun. 20, 2019

(87) PCT Pub. No.: WO2018/112625
PCT Pub. Date: Jun. 28, 2018

(65) Prior Publication Data
US 2019/0314643 A1    Oct. 17, 2019

Related U.S. Application Data

(60) Provisional application No. 62/437,295, filed on Dec. 21, 2016.

(51) Int. Cl.
*A61N 5/10* (2006.01)

(52) U.S. Cl.
CPC .... *A61N 5/1007* (2013.01); *A61N 2005/1008* (2013.01); *A61N 2005/1012* (2013.01); *A61N 2005/1094* (2013.01)

(58) Field of Classification Search
CPC ...... A61N 5/10; A61N 5/1001; A61N 5/1007; A61N 5/1027; A61N 2005/1012;
(Continued)

(56) References Cited

U.S. PATENT DOCUMENTS 5,800,333 A * 9/1998 Liprie ................. A61N 5/1007
600/3
2002/0115990 A1* 8/2002 Acker .................... A61N 7/022
606/27

(Continued)

FOREIGN PATENT DOCUMENTS

WO    2015039995    3/2015
WO    2017184728    10/2017

OTHER PUBLICATIONS

International Search Report and Written Opinion, issued in PCT application No. PCT/CA2017/051547, dated Feb. 8, 2018.

*Primary Examiner* — Samuel G Gilbert
(74) *Attorney, Agent, or Firm* — Norton Rose Fulbright Canada

(57) ABSTRACT

A delivery system and method for radiation shielded brachytherapy has a drive assembly, and a plurality of shield assemblies, pivotally mounted to the drive assembly, each having a tubular body defining an outer surface and a bore longitudinally extending between opposite ends of the tubular body. Each of the shield assemblies has radiation shielding material extending about a circumferential portion of the tubular body and disposed between the outer surface and the cavity. An interlocking system is operatively mounted to the rotating assembly, and engages a group of the plurality of shield assemblies. The interlocking system is configured for
(Continued)

transmitting a rotational input received from a driving mechanism to the group of shield assemblies, for synchronously rotating each shield assembly of the group about their respective longitudinal axis.

20 Claims, 5 Drawing Sheets

(58) Field of Classification Search
CPC .... A61N 2005/1008; A61N 2005/1094; A61N 2005/0612
See application file for complete search history.

(56) References Cited

U.S. PATENT DOCUMENTS

| | | |
|---|---|---|
| 2006/0235260 A1 | 10/2006 | Mourtada et al. |
| 2009/0216062 A1 | 8/2009 | Axelrod et al. |
| 2015/0367144 A1 | 12/2015 | Flynn et al. |
| 2019/0126064 A1* | 5/2019 | Flynn .................. A61N 5/1007 |

* cited by examiner

DELIVERY SYSTEM FOR INTENSITY MODULATED HIGH DOSE RATE BRACHYTHERAPY WITH INTERMEDIATE ENERGY BRACHYTHERAPY ISOTOPES

TECHNICAL FIELD

The application relates generally to apparatus and method for radiation therapy, more particularly, to brachytherapy.

BACKGROUND OF THE ART

Radiation therapy is known to be an effective treatment for cancer. New technology developments in external beam radiation therapy during the last decades have led to improvements in tailoring the dose distribution to the shape of the tumour and minimizing the dose to organs at risk. However, location of the tumour within the organ, errors in treatment delivery because of incorrect patient positioning, large margins and tumour/patient movement during the treatment can result in excessive doses to organs at risk. Delivery of a specified dose requires more monitor units and, as a consequence, the total body dose due to leakage radiation can be increased. This may lead to dose escalation, conformation and sharp dose gradients on one hand, while conversely they may increase the integral dose exposure of healthy tissues, since larger volumes are exposed to low doses.

The use of external radiation therapy may be limited in cases where the proximity of the tumour to radiation sensitive normal tissues makes it difficult to obtain an optimal absorbed dose distribution in the tumours area. Brachytherapy is thus desirable in these circumstances. High dose rate brachytherapy is a form of radiation therapy where radiation is administered from radiation sources (radionuclides) directly into or near the tumour, giving a high radiation dose to the target volume while sparing the surrounding radiation sensitive healthy tissues. The radionuclides are administered using an afterloading technique, where the applicator is first placed into the tumour and the radioactive sources are loaded later by a machine known as an afterloader.

Magnetic resonance imaging (MRI) guided brachytherapy provides good dose distributions in the tumour, with decreased margins and toxicity, due to excellent delineation of the tumour and surrounding tissue. The steep dose gradient from brachytherapy sources results in improved therapeutic ratio compared with external beam radiation therapy for selected tumour sites. However, optimal dose distribution in the tumour is limited in many tumour sites due to the proximity of the tumour to organs at risk, such as the urethra, rectum, urinary bladder and neurovascular bundle for prostate cancer. Other organs at risk are skin and axilla for breast cancer, bladder, rectum, sigmoid, and vagina for cervical and uterine cancer, urethra, rectum, bone, and skin for vaginal and vulvar cancer, salivary glands and mandible for head and neck cancer, and lung and spine for oesophageal cancer.

A radiation shield is therefore needed to protect organs at risk from excessive dose from brachytherapy sources. In Intensity Modulated brachytherapy (IMBT) shielded rotating catheters can be used to direct the radiation towards the tumour and away from the healthy tissues.

IMBT, designed and delivered with accurate anatomic reference, has the objective to tailor treatments to each individual patient by treating all parts of the tumour without needlessly irradiating large regions of organs at risk. With MRI guided IMBT the oncologist can identify where the cancer has spread, and instead of treating a large area around the tumour, they can fit the cell-killing treatments to the tumour.

SUMMARY OF THE INVENTION

There is accordingly provided, in accordance with one aspect of the present invention, a delivery system for radiation shielded brachytherapy, the delivery system being adapted to receive an input of radionuclide from an afterloader, the delivery system comprising: a drive assembly having a drive mechanism and connectors rotatable by the drive mechanism, each of the connectors having one of two or more shield assemblies detachably coupled thereto for rotation about a longitudinal axis of the respective shield assembly, each of the shield assemblies including a needle having a tubular body defining an outer surface and a bore longitudinally extending between opposite ends of the tubular body, the bore being adapted to receive therethrough the input of radionuclide for delivery to a target site, a radiation shielding material extending about a circumferential portion of the tubular body of the needle and disposed radially outwardly of the bore; and an interlocking system operatively mounted to the drive assembly, the interlocking system engaging a group of the two or more shield assemblies via their respective connectors, wherein the interlocking system transmits a rotational input received from the driving mechanism to the group of shield assemblies and synchronously rotates each of the shield assemblies of the group about its respective longitudinal axis.

In the delivery system as defined above, the interlocking system may comprise a fixed panel and a plurality of said connectors extending therethrough, the interlocking system comprising a moving panel operatively coupled to a group of said connectors engaging the group of the plurality of shield assemblies.

In the delivery system as defined above, each connector may define a transmitter and a coupler, the transmitter being received within a hole defined through the moving panel, an axis of rotation of the coupler is parallel but non-coaxial with an axis of rotation of the transmitter.

In the delivery system as defined above, the moving panel may be received within a recess of the fixed panel, the recess having a footprint greater than a footprint of the moving panel.

In the delivery system as defined above, the driving mechanism may comprise at least one electric motor operatively mounted to the rotating assembly.

In the delivery system as defined above, each of the shield assemblies may be operatively coupled to the drive assembly through a link assembly, the link assembly interconnecting a connector of the drive assembly and one of the shield assemblies.

In the delivery system as defined above, the link assembly may comprise a flexible luer.

In the delivery system as defined above, the shield assemblies may be connected to the drive assembly by respective flexible link assemblies, the longitudinal axis of each of the shield assemblies defines an angle with the respective connector of the rotating assembly, wherein each of the flexible link assemblies is independently bendable such that said angles of each of the shield assemblies is independently modifiable.

In the delivery system as defined above, the interlocking system may comprise a plurality of stages, each stage controlling a given group of the plurality of shield assemblies.

In the delivery system as defined above, the radiation shielding material may be non-uniformly circumferentially distributed around the bore.

In the delivery system as defined above, the radiation shielding material may extend longitudinally between the opposed ends of the tubular body.

There is also provided, in accordance with another aspect of the present invention, a method for directing radiation to target site of a tumour in brachytherapy, comprising: inserting a group of radiation shield assemblies proximate the tumour, the group of radiation shield assemblies each having a tubular body with a bore longitudinally extending therethrough along a longitudinal axis, a radiation shielding material extending about a circumferential portion of the tubular body; and synchronously rotating each of the radiation shield assemblies of the group about the respective longitudinal axis until the circumferential portion of at least one radiation shield assembly of the group is disposed on an opposite side of the tubular body from the target site of the tumour; and providing an input of radionuclide from an afterloader through the bore of the tubular body of said at least one shield assembly and directing the radiation from the input of radionuclide toward the target site of the tumour and restricting the radiation to the target site.

There is further provided, in accordance with another aspect of the present invention, a method for directing radiation to target site, comprising: providing a group of radiation shield assemblies and locating them proximate the target site, the group of radiation shield assemblies each having a tubular body with a bore longitudinally extending therethrough along a longitudinal axis, a radiation shielding material extending about a circumferential portion of the tubular body; and synchronously rotating each of the radiation shield assemblies of the group about the respective longitudinal axis until the circumferential portion of at least one radiation shield assembly of the group is disposed on an opposite side of the tubular body from the target site; and providing an input of radionuclide through the bore of the tubular body of said at least one shield assembly and directing the radiation generated by the radionuclide toward the target site and restricting the radiation to said target site.

The method(s) as defined above may further comprise independently rotating another group of the radiation shield assemblies with the driving mechanism until a circumferential portion comprising radiation shielding material of at least one shield assembly of the other group of the radiation shield assemblies faces away from the target site, and directing radiation received from a second input of the radionuclide toward the target site.

The method(s) as defined above may further comprise removing the radionuclide from the at least one radiation shield assembly before synchronously rotating said group until a circumferential portion comprising radiation shielding material of another shield assembly of said group faces away from the target site.

The method(s) as defined above may further comprise circumscribing the target site with the plurality of radiation shield assemblies.

The method(s) as defined above may further comprise synchronously rotating the radiation shield assemblies about their respective longitudinal axis until the circumferential portion having radiation shielding material of all of the radiation shield assemblies of said group faces away from the target site.

The method(s) as defined above may further comprise providing a drive assembly having a drive mechanism and connectors rotatable by the drive mechanism, and operatively coupling the radiation shield assemblies with the connectors of the drive mechanism using a link assembly.

The method(s) as defined above may further comprise absorbing any angular mismatch between the radiation shield assemblies and the connectors of the drive assembly using a flexible element in the link assembly.

The method(s) as defined above may further comprise independently bending each of the flexible elements of the link assembly to independently modify an angle between the longitudinal axis of the radiation shield assemblies and an axis of each respective connector of the drive assembly.

The method(s) as defined above may further comprise independently controlling each of two or more groups of the radiation shield assemblies.

BRIEF DESCRIPTION OF THE DRAWINGS

Reference is now made to the accompanying figures in which.

DETAILED DESCRIPTION

Figure 1:
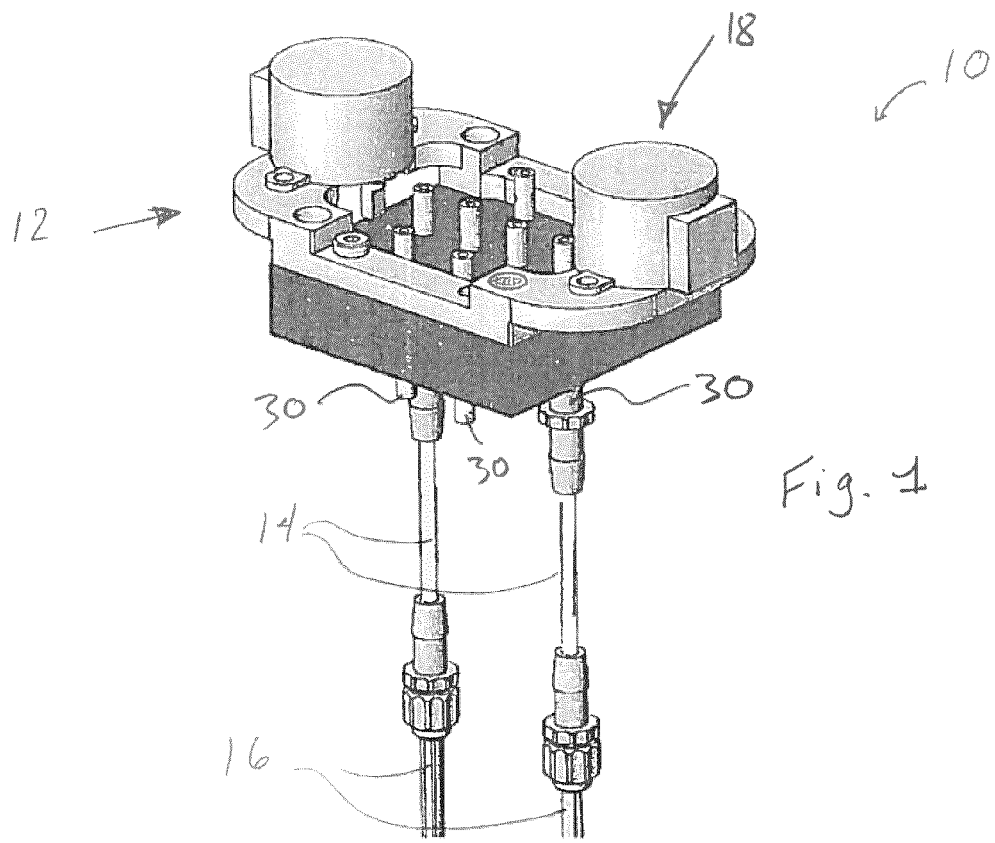
FIG. 1 is a perspective view of a delivery system in accordance with the present disclosure.
Figure 2:
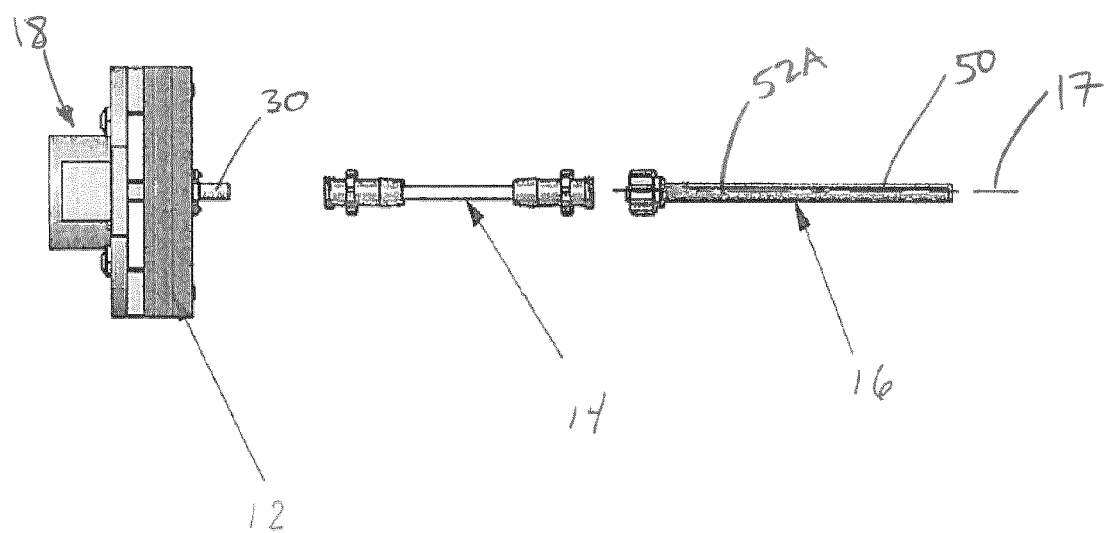
FIG. 2 is side partially exploded view of the delivery system of FIG. 1.
Figure 3:
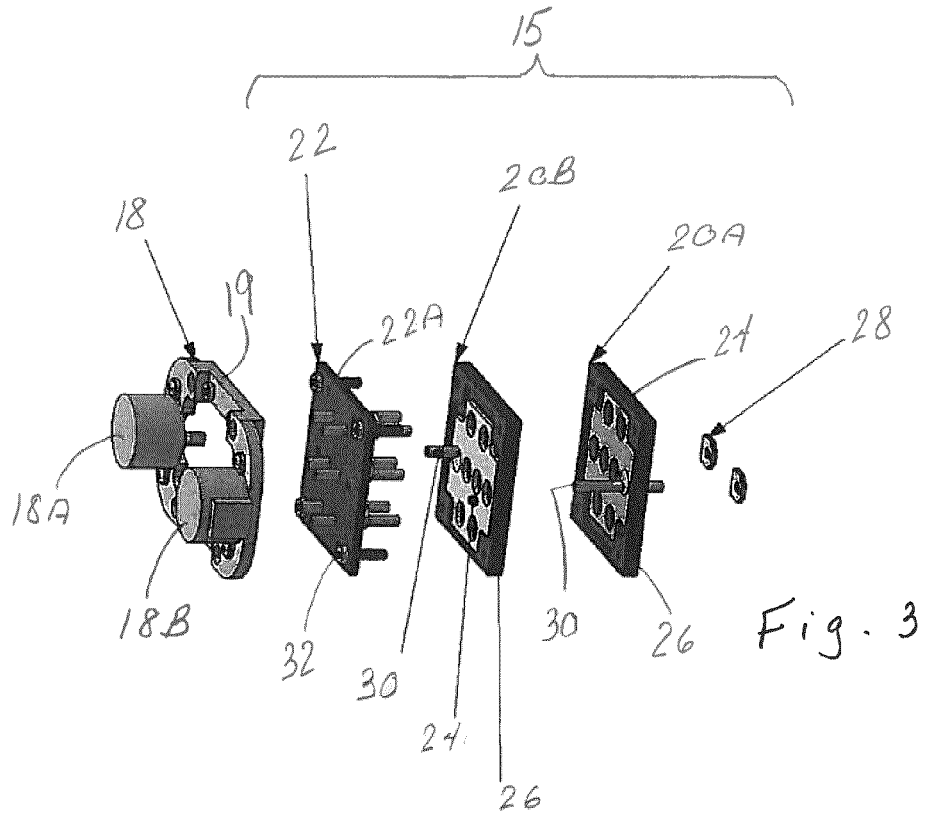
FIG. 3 is an exploded view of a rotating mechanism of the delivery system of FIG. 1.

Referring to FIGS. 1-3, a delivery system 10 for radiation shielded brachytherapy is adapted to receive an input of radionuclide from an afterloader (not shown). The system 10 comprises generally a drive assembly 12 (also referred to herein as a "rotating assembly" 12) and two or more shield assemblies 16 rotatably coupled to the drive assembly 12, as will be seen. In one particular embodiment, a link assembly 14 may be intermediately disposed between the drive assembly 12 and each of the shield assemblies 16. The link assembly 14 and the shield assemblies 16 will be discussed in further detail herein below.

As seen in FIGS. 1 and 2, the drive assembly 12 having a driving mechanism 18 and two or more connectors 30 rotatable by the driving mechanism 18, each of the connectors 30 having one of two or more shield assemblies 16 detachably coupled thereto for rotation about a longitudinal axis 17 of each respective shield assembly 16.

The shield assemblies 16 will be described in further detail below, particularly with reference to FIGS. 6A-6B, however each shield assembly 16 includes an outer needle having a tubular body 50 with a bore 52A (also referred to herein as a "cavity" 52A) longitudinally extending between opposite ends of the tubular body 50. The bore or cavity 52A is adapted to receive therethrough the input of radionuclide for delivery to a target site. A radiation shielding material (which may also be referred to herein as radiation opaque, radio opaque, or radiation attenuating) extends about a circumferential portion of the tubular body 50 of the needle and acts to shield predetermined regions of the patient's tissue from the radiation, depending on, among other things, the rotational position of the shield assemblies 16.

As seen in FIG. 3, the drive assembly 12 comprises an interlocking system 15 and a driving mechanism 18. The interlocking system 15 transmits a rotational input received from the driving mechanism 18 to a group of the plurality of shield assemblies 16. In one embodiment, the driving mechanism 18 comprises one or more electric motors 18A/B operatively mounted to a supporting plate 19. In another embodiment, rotational input may be provided by an electric motor not mounted directly to the system 10. In another embodiment, a manual system may be used for providing the rotational input.

Figure 4A:
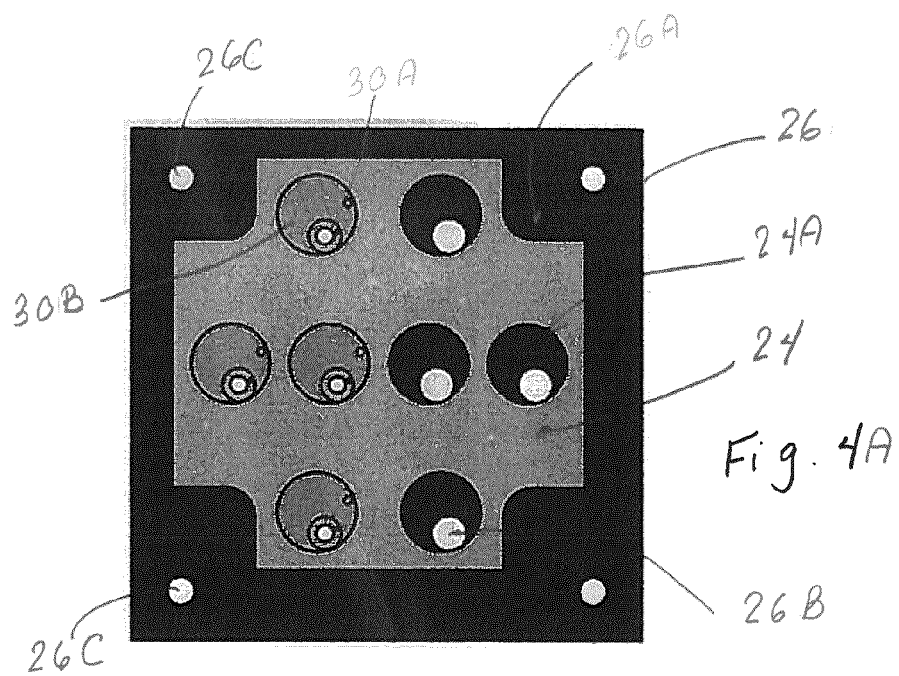
FIG. 4A is a top view of a portion of the rotating mechanism of FIG. 3.

Now referring to FIGS. 3 and 4 in more detail, the interlocking system 15 comprises a cover panel 22 and at least one driving stage 20A. The interlocking system 15 may however comprise two driving stages 20A and 20B or more. Each driving stage 20A/B comprises a fixed panel 26 and a moving panel 24. The fixed panel defines a recess 26A within its thickness for receiving the moving panel 24. The recess 26A has a depth adjusted in accordance with the thickness of the moving panel 24 and is sized to allow for movement of the moving panel 24 within the recess 26A. The recess 26A defines a shape substantially corresponding to a shape of the moving panel 24. A perimeter of the recess 26A is however greater than a perimeter of the moving panel 24 thereby allowing translational movements of the moving panel 24 within the recess 26A.

The moving panel 24 defines a plurality of apertures 24A adapted for receiving transmitters 30B of connectors 30. The connectors 30 are also referred to herein as crank shafts. Each crank shaft 30 also comprises a coupler 30A. In one embodiment, the transmitters 30B are cylindrical portions and the couplers 30A are cylinders longitudinally extending through the transmitters 30B. An axis of rotation of a transmitter 30B is parallel to but not coincident with, an axis of rotation of its associated coupler 30A. The transmitter 30B and the coupler 30A are parallel but eccentric. In a particular embodiment, a diameter of the coupler 30A is smaller than a diameter of the transmitter 30B. A peripheral surface of a transmitter 30B is in contact with a peripheral surface of its receiving aperture 24A of the moving panel 24 and allows rotational movements therebetween. In another embodiment, a bearing may be disposed between the transmitter 30B and the aperture 24A.

Each connector 30 defines a hollow section longitudinally extending along its axis of rotation through both the coupler 30A and the transmitter 30B. The hollow section permits the insertion of a source of radionuclide from an afterloader.

The plate 19, the cover panel 22 and each of the stages 20A/B of the interlocking system 15 are assembled in a stacked relationship. In one embodiment, the fixed panel 26 defines holes 26C adapted for receiving fasteners 32 used to secure the interlocking system 15 together. Understandably, any other means adapted for maintaining the cover panel 22 and the stages 20A/B together with the plate 19 may be used. The couplers 30A are adapted to extend from both sides of the transmitters 30B through the cover panel 22 and through each stage 20A/B through holes 22A and 26B when the interlocking system 15 is assembled. At least one coupler 30A extending from the cover 22 is adapted to receive the rotational input from the driving mechanism 18. The portions extending in the opposite direction, from the last stage, will engage the linking assemblies 14.

Figure 4B:
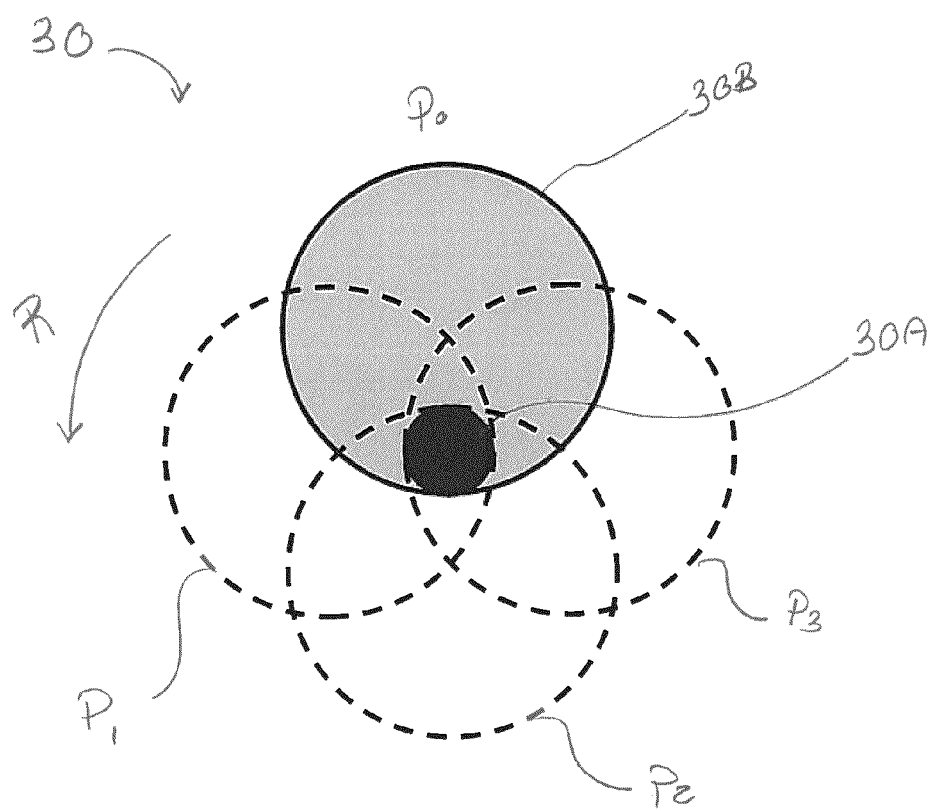
FIG. 4B is a schematic top view of the positions of the connector of the rotating mechanism of FIG. 3.

Now referring to FIG. 4B, a coupler 30A is pivotally received within a hole 26B defined through the fixed panel 26 and rotates therein. As aforementioned, the respective transmitter 30B is eccentric relative to the coupler 30A. Consequently, rotation of the coupler 30A along direction R induces a translation of the transmitter 30B around the coupler 30A because of their eccentricity. The translation defines a circular movement in which the transmitter 30B moves from its initial position $P_0$, to the next position $P_1$ and successively to positions $P_2$ and $P_3$ to finally return to the initial position $P_0$. The moving panel 24 will thus follow the same circular translation since it pivotally receives the transmitter 30B. The moving panel 24 then induces the same circular translation to other transmitter 30B pivotally received therein. Thus, two couplers 30A having their respective transmitter 30B pivotally received within the same moving panel 24 rotate synchronously. Understandably, the system may rotate in both directions.

The rotating assembly 12 further comprising sensors 28. In a particular embodiment, the electric motors 18A/B in the driving mechanism are equipped with controller sensors 28 that are operable to control the motor position. Other sensors (not illustrated) may also be provided and are configured to read the real position of the shield assembly and provide the information to the controller sensors 28, which will adjust the rotation of the shield assembly. In a particular embodiment, the other sensors are placed directly on the shield assembly. In an alternate embodiment, the other sensors are placed adjacent to the end of the link assembly. The sensors are operatively connected with one another and with the electric motors.

The rotational input is transferred from the driving mechanism 18 to one of the connectors 30 directly or indirectly through a transmission mechanism (not shown). A gear or drive train mechanism may be used for that purpose. Rotation of the connector 30 will induce movement of the moving panel 24 within the recess 26A because of the non-coaxiality of the couplers 30A and transmitters 30B. By moving, the panel 24 will thus impose the same movement to each of the other connectors 30 whose transmitters 30B are disposed in an aperture 24A of said moving panel 24 thereby providing rotational synchronization to each of the connectors 30, and thus each of the shield assembly 16 connected to the moving panel 24.

In some applications, it may be required to have a group of connectors moving independently than the other connectors. This may be the case, for example, if an afterloader provides two sources of radionuclides. To independently control rotation of two groups of connectors 30, a second stage 20B is added to the interlocking system 15. In the case where only two stages 20A/B are present, a first group of connectors 30 will have their transmitters 30B operatively coupled to the moving panel 24 of the first stage 20A while a second group of connectors 30 will have their transmitters 30B operatively coupled to the moving panel 24 of the second stage 20B.

In one embodiment, each stage 20A/B is in a driving engagement with an electric motor 18A/B. In another embodiment, only one electric motor may be provided to drive all stages 20A/B, regardless of the number of stages. A selector may thus be mounted on the driving mechanism 18 for selectively engaging the desired stage 20A/B and/or the desired electric motor 18A/B. However, if both groups of connectors 30 are to be independently controlled and moved at the same time, one electric motor for each stage may need to be used.

The interlocking system 15 is not limited to the embodiment of moving and fixed panels. For example, gears may be operatively mounted within the recess of the fixed panel for transmitting the movement of a connector to the other connectors. The gears may also be replaced by a strap and pulley system.

Figure 5:
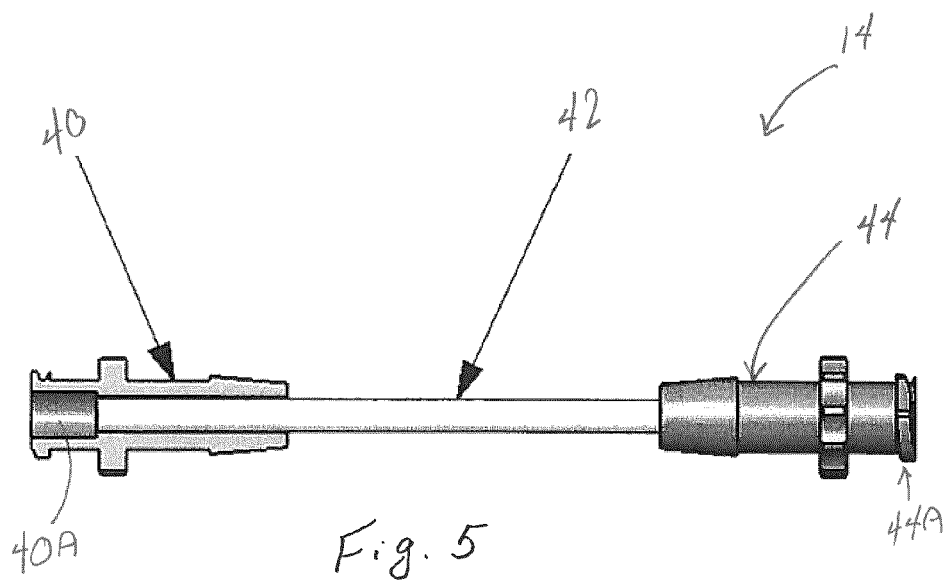
FIG. 5 is a partially transparent view of a linking assembly of the delivery system of FIG. 1.

Now referring to FIG. 5, the link assembly 14 is adapted to be disposed between a connector 30 and a shield assembly 16. The link assembly 14 comprises a hollow tube 42 having two luers 40 and 44 operatively coupled to both of its ends. The first luer 40 is adapted to be engaged by a coupler 30A of a connector 30. In a specific embodiment, the luer is provided with an aperture 40A having a diameter equal to or slightly smaller than the external diameter of the coupler 30A to provide a tight fit engagement therebetween. The other luer 44 may use its external threaded surface 44A to engage a corresponding internal surface of an extremity 46 of a shield assembly 16. Other means for engaging the luers with the connectors 30 or the shield assembly 16 may also be used without departing from the scope of the present disclosure. In one embodiment, the tube 42 is flexible, thereby permitting the link assembly 14 to bend and thus accommodate angular misalignment between the shield assembly 16 and the connector 30. This flexibility may help a physician to more precisely insert the shield assembly 16 proximate to the tumour. The flexibility may also allow the shield assembly 16 to penetrate the patient at a selected angle, which may differ from an angle of penetration of the other shield assemblies 16. As such, if required, each of the shield assemblies 16 can be disposed at a different angular position, while the system is still able to rotate the shield assemblies 16 as required.

Figure 6A:
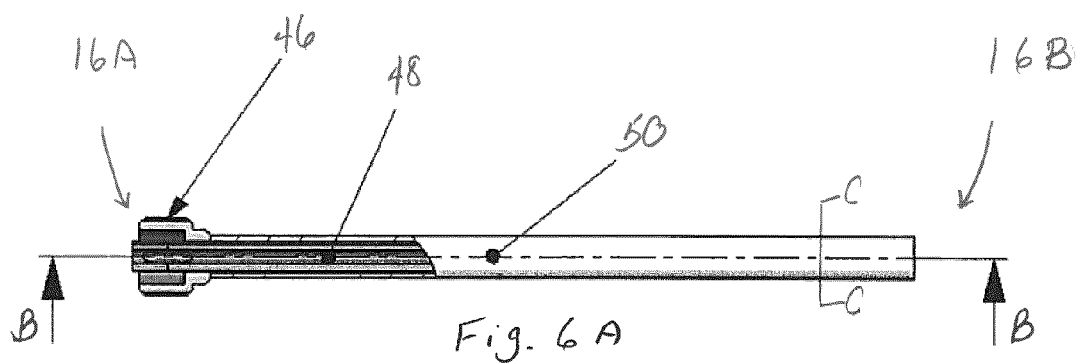
FIG. 6A is a partially transparent view of a shield assembly of the delivery system of FIG. 1.
Figure 6B:
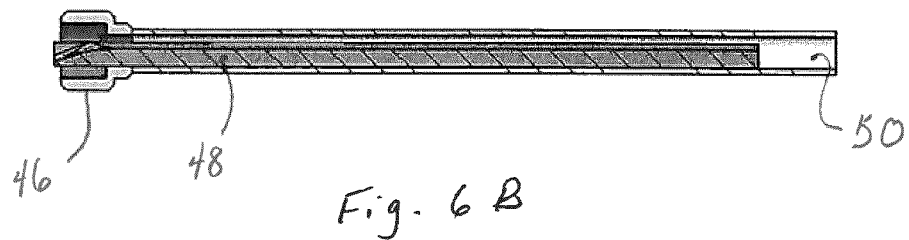
FIG. 6B is a view along line B-B of FIG. 6A.
Figure 6C:
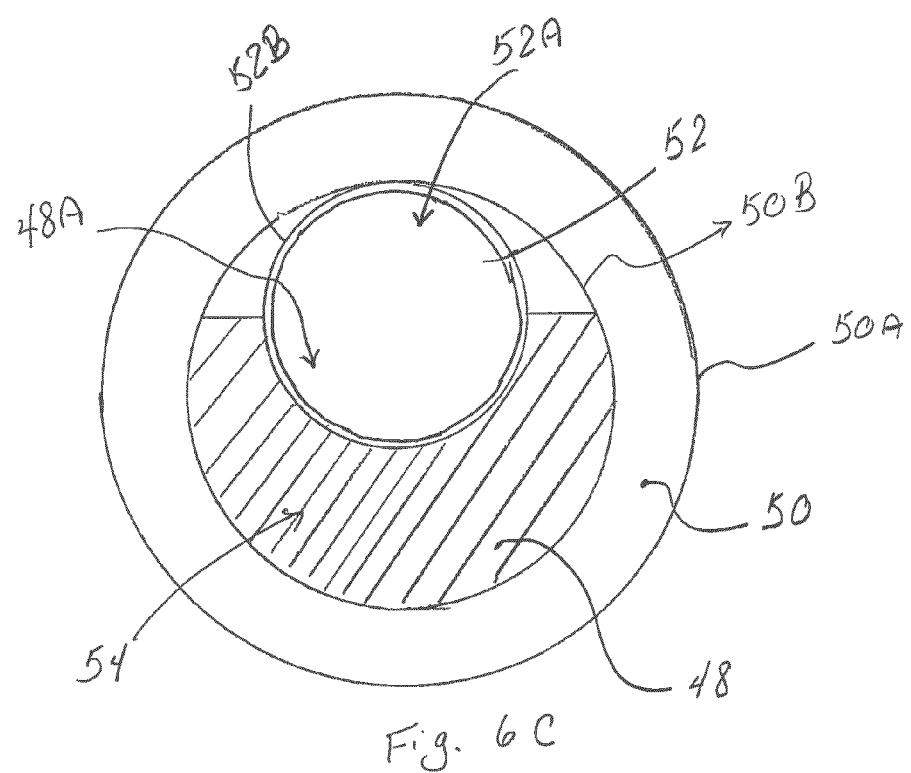
FIG. 6C is a view along line C-C of FIG. 6A.

Now referring to FIGS. 6A to 6C, the shield assembly 16 comprises a coupling end 46 adapted to be engaged by the luer 40 or 44. The coupling end 46 is operatively coupled to a tubular body, or a cylindrical needle 50. In one embodiment, the needle is made from a plastic material, including for example nitinol. However, any other suitable material known in the art may be used.

Each shield assembly 16 comprises a tubular body 50 extending between opposite ends 16A and 16B of the assembly 16 and defines an outer cylindrical surface 50A and an inner cylindrical surface 50B. The inner cylindrical surface 50B corresponds to a peripheral wall of a hollow portion 54 of the tubular body 50. The tubular body 50 receives another tubular body 52 within its hollow portion 54. The tubular body 52 defines a cavity 52A longitudinally extending between the opposite ends 16A and 16B. The tubes 50 and 52, and thus the cavity 52A therewithin, may accordingly shift and bend as required away from the longitudinal central axis of the tubular body 50 extending through the end 16A. In such a bent or curved configuration, the longitudinal central axis may thus be parallel, but not co-axial, with the original axis of the non-deformed shield assembly 16. The cavity 52A is adapted to receive an input of radionuclide provided by an afterloader (not shown).

The hollow portion 54 receives radiation shielding material 48 that is disposed between both tubular bodies 50 and 52. The radiation shielding material 48 extends about a circumferential portion of the tubular body. The radiation shielding material may be, but not limited to, platinum. In a particular embodiment, the radiation shielding material is non-uniformly circumferentially distributed around the cavity 52A. In another particular embodiment, the radiation shielding material extends longitudinally between the opposite ends 16A and 16B of the assembly 16.

In a particular embodiment, the radiation shielding material 48 is substantially radiation opaque and at least partially surrounds the tubular body 52, thereby providing a portion free of radiation shielding material 52B that creates a path for the radiation to escape the shield assembly 16 to irradiate the tumour. The quantity of shielding material 48 disposed in the hollow portion 54 may be varied using methods known in the art for tuning a radiation emission angle. In a particular embodiment, the radiation shielding material 48 defines a concave portion 48A for receiving a portion of the tubular body 52. Different types of shield assemblies 16 may be used regarding a plurality of factors, such as the intensity of the radiation, the type of cancer, and the size of the tumour.

The connectors 30, the link assemblies 14 and the shield assemblies 16 all define a longitudinally extending hollow portion for receiving the input of radionuclide from the afterloader. The intensity of the radionuclide has to be carefully selected based on the diameter of the needle 50. For instance, when the needle is inserted in the body, a source of radionuclide being on intermediate-energy level may be used, because the needle may not comprise sufficient radiation shielding material to provide efficient protection of healthy tissues for high-energy level radionuclides.

Typically, brachytherapy can be administered by low-energy ($^{125}$I and $^{103}$Pd, E<50 keV), intermediate energy ($^{169}$Yb, 50 keV <E<200 keV) or high-energy ($^{192}$Ir, E>200 keV) gamma emitting radionuclides. Brachytherapy sources are inserted into a patient's tissue where the space available for applicators is limited. The thickness of the shield must be in the sub-millimeter range to fit inside existing brachytherapy catheters and yet modify the intensity of the source by several half-value layers. Sub millimetre of a dense metal can shield photons from the intermediate energy brachytherapy sources while several millimetres are needed to shield high-energy sources such as $^{192}$Ir. For $^{192}$Ir the shield would not fit inside the shield assembly 16. It is understood that the present system may be scaled up and may be used to treat intracavitary cancers, such as, but not limited to, vaginal cancer and rectal cancer. In such a case, the shields may be thicker and high energy sources may be consequently used.

Figure 7:
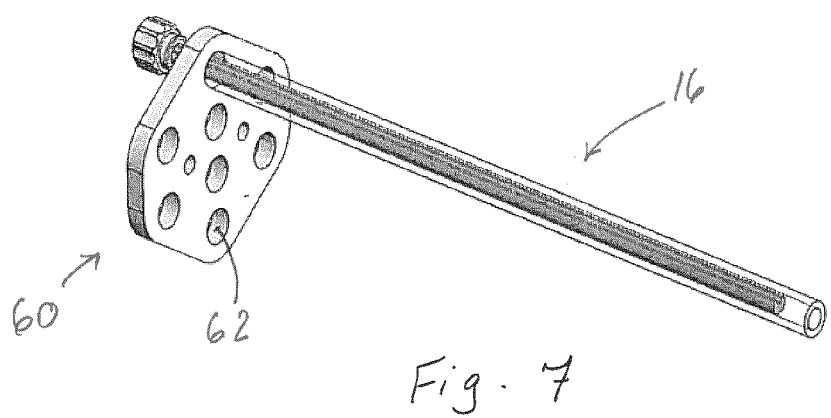
FIG. 7 is a perspective view of a distribution template for supporting the shield assemblies.

Now referring to FIG. 7, a guide template 60 is illustrated which may be used in conjunction with the shield assemblies 16. The guide template 60 has a number of apertures 62 which are each sized to receive a shield assembly 16 therein. This guide template 60 may facilitate manipulation of the device 10 and insertion of the needles 50 within a patient. Typically, the guide template may be selected according to a shape of a tumour or a type of cancer to be treated.

Although the present embodiment has been described as having two stages, two electric motors, and comprising eight connectors and shield assemblies, it may be configured to comprise more or less stages, more or less electric motors, and more or less connectors. The template may also be changed such that its shape substantially matches the shape of a tumour. It may also be possible to manufacture a device comprising any number of connectors 30 and to use only the connectors required for a given type of cancer or tumour shape such that only one device would be configured to match the size and shape of any tumours.

A method for treating a tumour using radiation shielded brachytherapy is also disclosed. The method comprises the step of inserting a group of a plurality of shield assemblies 16 into a target site proximate to the tumour. The group of shield assemblies 16 are pivotally coupled to a rotating assembly 12 and each has a tubular body 50 defining an outer surface and a cavity 52A longitudinally extending between opposite ends of the tubular body 50. Each of the plurality of shield assemblies 16 comprise radiation shielding material 48 that extend about a circumferential portion of the tubular body 50 and disposed between the outer surface and the cavity 52A.

The method further comprises the step of synchronously rotating each shield assembly 16 of the group of the plurality of shield assemblies about their longitudinal axis with an interlocking system 15 that receives a rotational input from a driving mechanism 18. The rotation is carried until the radiation shielding material 48 of at least one shield assembly 16 of the group of the plurality of shield assemblies faces away from a target site, thereby directing radiation received from at least one input of radionuclide toward the target site and thereby substantially restricting the radiation to this target site (by substantially preventing the radiation from irradiating the regions outside the target site that are shielded by the radiation shielding material 48 of the shield assemblies). The "target site" as defined herein may include both an in vivo target area of a tumour or another affected tissue area, for example, and an in vitro target—whether human cells or not. Thus, the present method may be used as method of medical treatment for irradiating tumours, but may also be used to direct radiation to a non-human cell target site in an ex vivo and/or in vitro context.

The plurality of shield assemblies 16 may comprise one or more groups each operatively coupled to a stage 20 of the interlocking system 15. In one embodiment, each stage 20A and 20B is drivingly engaged by an electric motor 18A and 18B mounted on a plate or frame 19.

The method may further comprise the step of circumscribing the tumour with the plurality of shield assemblies 16 by inserting the tubular bodies, or needles 50 of each shield assembly 16 inside a patient. Once the radiation shielding material 48 of at least one shield assembly 16 is rotated and faces away from the target area of the tumour, an input of radionuclides is inserted in a hollow portion of a connector 30 that is connected to the at least one shield assembly 16 and inside the patient for irradiating the tumour. In a particular embodiment, the input of radionuclides passes through the connector 30, to the link assembly 14, and through the cavity 52A of the tubular body 50 of the shield assembly 16. A dummy source may be used to ensure that the input of radionuclide will be able to pass through the system and does not get stocked inside the patient.

The method may further comprise withdrawing the source of radionuclides from the at least one shield assembly 16 and rotating another shield assembly 16 operatively coupled to either one of the stage 20A or 20B using the corresponding motor 18A or 18B until a circumferential portion comprising radiation shielding material faces away from the target area of the tumour. Then, the input of radionuclides is inserted inside the other one of the group for irradiating the tumour.

If more than one shield assemblies 16 have their radiation shielding material facing away from the target area of the tumour, the input of radionuclide may be withdrawn from one assembly 16 and inserted in another without rotation.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A delivery system for radiation shielded brachytherapy, the delivery system being adapted to receive an input of radionuclide from an afterloader, the delivery system comprising:
    a drive assembly having a drive mechanism and connectors rotatable by the drive mechanism, each of the connectors having one of two or more shield assemblies detachably coupled thereto for rotation about a longitudinal axis of the respective shield assembly, each of the shield assemblies including a needle having a tubular body defining an outer surface and a bore longitudinally extending between opposite ends of the tubular body, the bore being adapted to receive therethrough the input of radionuclide for delivery to a target site, a radiation shielding material extending about a circumferential portion of the tubular body of the needle and disposed radially outwardly of the bore; and
    an interlocking system operatively mounted to the drive assembly, the interlocking system engaging a group of the two or more shield assemblies via their respective connectors, wherein the interlocking system transmits a rotational input received from the drive mechanism to the group of shield assemblies and synchronously rotates each of the shield assemblies of the group about its respective longitudinal axis,
    wherein the interlocking system comprises a plurality of stages, each stage controlling a given group of the two or more shield assemblies.

2. The delivery system of claim 1, wherein the interlocking system comprises a fixed panel and a plurality of said connectors extending therethrough, the interlocking system comprising a moving panel operatively coupled to a group of said connectors engaging the group of the two or more shield assemblies.

3. The delivery system of claim 2, wherein each connector defines a transmitter and a coupler, the transmitter being received within a hole defined through the moving panel, an axis of rotation of the coupler is parallel but non-coaxial with an axis of rotation of the transmitter.

4. The delivery system of claim 3, wherein the moving panel is received within a recess of the fixed panel, the recess having a footprint greater than a footprint of the moving panel.

5. The delivery system of claim 1, wherein the drive mechanism comprises at least one electric motor operatively mounted to the drive assembly.

6. The delivery system of claim 1, wherein each of the shield assemblies is operatively coupled to the drive assembly through a link assembly, the link assembly interconnecting a connector of the drive assembly and one of the shield assemblies.

7. The delivery system of claim 6, wherein the link assembly comprises a flexible luer.

8. The delivery system of claim 1, wherein the shield assemblies are connected to the drive assembly by respective flexible link assemblies, the longitudinal axis of each of the shield assemblies defines an angle with the connector of the drive assembly, wherein each of the flexible link assemblies is independently bendable such that said angles of each of the shield assemblies is independently modifiable.

9. The delivery system of claim 1, wherein the radiation shielding material is non-uniformly circumferentially distributed around the bore.

10. The delivery system of claim 1, wherein the radiation shielding material extends longitudinally between the opposite ends of the tubular body.

11. A method for directing radiation to target site of a tumour in brachytherapy, comprising:
inserting a group of radiation shield assemblies proximate the tumour, the group of radiation shield assemblies each having a tubular body with a bore longitudinally extending therethrough along a longitudinal axis, a radiation shielding material extending about a circumferential portion of the tubular body; and
synchronously rotating each of the radiation shield assemblies of the group about the respective longitudinal axis until the circumferential portion of at least one radiation shield assembly of the group is disposed on an opposite side of the tubular body from the target site of the tumour;
providing an input of radionuclide from an afterloader through the bore of the tubular body of said at least one shield assembly and directing radiation from the input of radionuclide toward the target site of the tumour and restricting the radiation to the target site; and
independently rotating another group of the radiation shield assemblies until a circumferential portion comprising radiation shielding material of at least one shield assembly of the other group of the radiation shield assemblies faces away from the target site, and directing radiation received from a second input of the radionuclide toward the target site.

12. The method of claim 11, further comprising removing the radionuclide from the at least one radiation shield assembly before synchronously rotating said group until a circumferential portion comprising radiation shielding material of another shield assembly of said group faces away from the target site.

13. The method of claim 11, further comprising circumscribing the target site with two or more radiation shield assemblies.

14. The method of claim 13, further comprising synchronously rotating the radiation shield assemblies about their respective longitudinal axis until the circumferential portion having radiation shielding material of all of the radiation shield assemblies of said group faces away from the target site.

15. The method of claim 11, further comprising providing a drive assembly having a drive mechanism and connectors rotatable by the drive mechanism, and operatively coupling the radiation shield assemblies with the connectors of the drive mechanism using a link assembly.

16. The method of claim 15, further comprising absorbing any angular mismatch between the radiation shield assemblies and the connectors of the drive assembly using a flexible element in the link assembly.

17. The method of claim 16, further comprising independently bending each of the flexible elements of the link assembly to independently modify an angle between the longitudinal axis of the radiation shield assemblies and an axis of each respective connector of the drive assembly.

18. The method of claim 11, further comprising independently controlling each of two or more groups of the radiation shield assemblies.

19. A delivery system for radiation shielded brachytherapy, the delivery system being adapted to receive an input of radionuclide from an afterloader, the delivery system comprising:
a drive assembly having a drive mechanism and connectors rotatable by the drive mechanism, each of the connectors having one of two or more shield assemblies detachably coupled thereto for rotation about a longitudinal axis of the respective shield assembly, each of the shield assemblies including a needle having a tubular body defining an outer surface and a bore longitudinally extending between opposite ends of the tubular body, the bore being adapted to receive therethrough the input of radionuclide for delivery to a target site, a radiation shielding material extending about a circumferential portion of the tubular body of the needle and disposed radially outwardly of the bore; and
an interlocking system operatively mounted to the drive assembly, the interlocking system engaging a group of the two or more shield assemblies via their respective connectors, wherein the interlocking system transmits a rotational input received from the drive mechanism to the group of shield assemblies and synchronously rotates each of the shield assemblies of the group about its respective longitudinal axis,
wherein the shield assemblies are connected to the drive assembly by respective flexible link assemblies, the longitudinal axis of each of the shield assemblies defines an angle with the connector of the drive assembly, wherein each of the flexible link assemblies is independently bendable such that said angles of each of the shield assemblies is independently modifiable.

20. The delivery system of claim 19, wherein the interlocking system comprises a fixed panel and a plurality of said connectors extending therethrough, the interlocking system comprising a moving panel operatively coupled to a group of said connectors engaging the group of the two or more shield assemblies.

* * * * *